(12) United States Patent
Fuisz et al.

(10) Patent No.: US 7,972,618 B2
(45) Date of Patent: Jul. 5, 2011

(54) EDIBLE WATER-SOLUBLE FILM CONTAINING A FOAM REDUCING FLAVORING AGENT

(75) Inventors: Richard C. Fuisz, McLean, VA (US); Joseph M. Fuisz, Washington, DC (US); Garry L. Myers, Kingsport, TN (US)

(73) Assignee: MonoSol Rx, LLC, Portage, IN (US)

( * ) Notice: Subject to any disclaimer, the term of this patent is extended or adjusted under 35 U.S.C. 154(b) by 112 days.

(21) Appl. No.: 11/858,214

(22) Filed: Sep. 20, 2007

(65) Prior Publication Data

US 2008/0075825 A1 Mar. 27, 2008

Related U.S. Application Data

(60) Provisional application No. 60/846,064, filed on Sep. 20, 2006.

(51) Int. Cl.
*A61K 47/00* (2006.01)
(52) U.S. Cl. ........................... 424/439; 424/400
(58) Field of Classification Search .................. None
See application file for complete search history.

(56) References Cited

U.S. PATENT DOCUMENTS

| | | | |
|---|---|---|---|
| 307,537 A | 11/1884 | Foulks |
| 688,446 A | 12/1901 | Stempel |
| 2,142,537 A | 1/1939 | Tisza |
| 2,277,038 A | 3/1942 | Curtis |
| 2,352,691 A | 7/1944 | Curtis |
| 2,501,544 A | 3/1950 | Shrontz |
| 2,980,554 A | 4/1961 | Gentile et al. |
| 3,007,848 A | 11/1961 | Stroop |
| 3,249,109 A | 5/1966 | Maeth et al. |
| 3,444,858 A | 5/1969 | Russell |
| 3,536,809 A | 10/1970 | Applezweig |
| 3,551,556 A | 12/1970 | Kliment et al. |
| 3,598,122 A | 8/1971 | Zaffaroni |
| 3,632,740 A | 1/1972 | Robinson et al. |
| 3,640,741 A | 2/1972 | Etes |
| 3,641,237 A | 2/1972 | Gould et al. |
| 3,731,683 A | 5/1973 | Zaffaroni |
| 3,753,732 A | 8/1973 | Boroshok |
| 3,814,095 A | 6/1974 | Lubens |
| 3,840,657 A * | 10/1974 | Norfleet .................... 424/49 |
| 3,892,905 A | 7/1975 | Albert |
| 3,911,099 A | 10/1975 | DeFoney et al. |

(Continued)

FOREIGN PATENT DOCUMENTS

| | | |
|---|---|---|
| EP | 0200508 A2 | 12/1986 |
| EP | 0241178 A1 | 10/1987 |
| EP | 0250187 A2 | 12/1987 |

(Continued)

OTHER PUBLICATIONS

Lazaridou et al.; Thermophysical properties of chitosan, chitosan-starch and chitosan-pullulan films near the glass transition; Elsevier Science Ltd.; 2002; pp. 179-190.
English translation of a portion of JP2001-279100A.
Lazaridou et al., "Thermophysical properties of chitosan, chitosan-starch and chitosan-pullulan films near the glass transition," Carbohydrate Polymers 48: 179-190 (2002).
Repka et al., "Bioadhesive properties of hydroxypropylcellulose topical films produced by hot-melt extrusion," Journal of Controlled Release 70: 341-351 (2001).
Repka et al., "Influence of Vitamin E TPGS on the properties of hydrophilic films produced by hot-melt extrusion," International Journal of Pharmaceutics 202: 63-70 (2000).
International Search Report from PCT/US2004/002602, dated Jul. 21, 2004.

*Primary Examiner* — Anand Desai
*Assistant Examiner* — Melissa Mercier
(74) *Attorney, Agent, or Firm* — Hoffmann & Baron, LLP

(57) ABSTRACT

An edible water-soluble film is provided. The film includes at least one water-soluble polymer, and a foam reducing flavoring agent, wherein the film is free of added anti-foaming or defoaming agents.

5 Claims, 6 Drawing Sheets

U.S. PATENT DOCUMENTS

| | | | |
|---|---|---|---|
| 3,972,995 A | 8/1976 | Tsuk et al. |
| 3,996,934 A | 12/1976 | Zaffaroni |
| 3,998,215 A | 12/1976 | Anderson et al. |
| 4,029,757 A | 6/1977 | Mlodozeniec et al. |
| 4,029,758 A | 6/1977 | Mlodozeniec et al. |
| 4,031,200 A | 6/1977 | Reif |
| 4,123,592 A | 10/1978 | Rainer et al. |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,226,848 A | 10/1980 | Nagai et al. |
| 4,251,400 A | 2/1981 | Columbus |
| 4,292,299 A | 9/1981 | Suzuki et al. |
| 4,294,820 A | 10/1981 | Keith et al. |
| 4,302,465 A | 11/1981 | Ekenstam et al. |
| 4,307,075 A | 12/1981 | Martin |
| 4,325,855 A | 4/1982 | Dickmann |
| 4,373,036 A | 2/1983 | Chang et al. |
| 4,406,708 A | 9/1983 | Hesselgren |
| 4,432,975 A | 2/1984 | Libby |
| 4,438,258 A | 3/1984 | Graham |
| 4,460,562 A | 7/1984 | Keith et al. |
| 4,466,973 A | 8/1984 | Rennie |
| 4,503,070 A | 3/1985 | Eby |
| 4,515,162 A | 5/1985 | Yamamoto et al. |
| 4,517,173 A | 5/1985 | Kizawa et al. |
| 4,529,601 A | 7/1985 | Broberg et al. |
| 4,529,748 A | 7/1985 | Wienecke |
| 4,562,020 A | 12/1985 | Hijiya et al. |
| 4,569,837 A | 2/1986 | Suzuki et al. |
| 4,593,053 A | 6/1986 | Jevne |
| 4,608,249 A | 8/1986 | Otsuka et al. |
| 4,615,697 A | 10/1986 | Robinson |
| 4,623,394 A | 11/1986 | Nakamura et al. |
| 4,631,837 A | 12/1986 | Magoon |
| 4,652,060 A | 3/1987 | Miyake |
| 4,659,714 A | 4/1987 | Watt-Smith |
| 4,675,009 A | 6/1987 | Hymes et al. |
| 4,695,465 A | 9/1987 | Kigasawa et al. |
| 4,704,119 A | 11/1987 | Shaw et al. |
| 4,713,239 A | 12/1987 | Babaian et al. |
| 4,713,243 A | 12/1987 | Schiraldi et al. |
| 4,722,761 A | 2/1988 | Cartmell et al. |
| 4,740,365 A | 4/1988 | Yukimatsu et al. |
| 4,748,022 A | 5/1988 | Busciglio |
| 4,765,983 A | 8/1988 | Takayanagi et al. |
| 4,772,470 A | 9/1988 | Inoue et al. |
| 4,777,046 A | 10/1988 | Iwakura et al. |
| 4,789,667 A | 12/1988 | Makino et al. |
| 4,849,246 A | 7/1989 | Schmidt |
| 4,860,754 A | 8/1989 | Sharik et al. |
| RE33,093 E | 10/1989 | Schiraldi et al. |
| 4,876,092 A | 10/1989 | Mizobuchi et al. |
| 4,876,970 A | 10/1989 | Bolduc |
| 4,888,354 A | 12/1989 | Chang et al. |
| 4,894,232 A | 1/1990 | Reul et al. |
| 4,900,552 A | 2/1990 | Sanvordeker et al. |
| 4,900,554 A | 2/1990 | Yanagibashi et al. |
| 4,900,556 A | 2/1990 | Wheatley et al. |
| 4,910,247 A | 3/1990 | Haldar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki et al. |
| 4,981,693 A | 1/1991 | Higashi et al. |
| 4,981,875 A | 1/1991 | Leusner et al. |
| 5,023,082 A | 6/1991 | Friedman et al. |
| 5,024,701 A | 6/1991 | Desmarais |
| 5,028,632 A | 7/1991 | Fuisz |
| 5,047,244 A | 9/1991 | Sanvordeker et al. |
| 5,064,717 A | 11/1991 | Suzuki et al. |
| 5,089,307 A | 2/1992 | Ninomiya et al. |
| 5,158,825 A | 10/1992 | Altwirth |
| 5,166,233 A | 11/1992 | Kuroya |
| 5,186,938 A | 2/1993 | Sablotsky et al. |
| 5,229,164 A | 7/1993 | Pins et al. |
| 5,234,957 A | 8/1993 | Mantelle |
| 5,271,940 A | 12/1993 | Cleary et al. |
| 5,272,191 A | 12/1993 | Ibrahim et al. |
| 5,346,701 A | 9/1994 | Heiber et al. |
| 5,354,551 A | 10/1994 | Schmidt |
| 5,393,528 A | 2/1995 | Staab |
| 5,411,945 A | 5/1995 | Ozaki et al. |
| 5,413,792 A | 5/1995 | Ninomiya et al. |
| 5,433,960 A | 7/1995 | Meyers |
| 5,455,043 A | 10/1995 | Fischel-Ghodsian |
| 5,462,749 A | 10/1995 | Rencher |
| 5,472,704 A | 12/1995 | Santus et al. |
| 5,518,902 A | 5/1996 | Ozaki et al. |
| 5,567,431 A | 10/1996 | Vert et al. |
| 5,605,696 A | 2/1997 | Eury et al. |
| 5,620,757 A | 4/1997 | Ninomiya et al. |
| 5,629,003 A | 5/1997 | Horstmann et al. |
| 5,698,181 A * | 12/1997 | Luo ............................... 424/49 |
| 5,700,478 A | 12/1997 | Biegajski et al. |
| 5,700,479 A | 12/1997 | Lundgren |
| 5,766,620 A | 6/1998 | Heiber et al. |
| 5,800,832 A | 9/1998 | Tapolsky et al. |
| 5,806,284 A | 9/1998 | Gifford |
| 5,948,430 A | 9/1999 | Zerbe et al. |
| 6,072,100 A | 6/2000 | Mooney et al. |
| 6,153,210 A | 11/2000 | Roberts et al. |
| 6,177,096 B1 | 1/2001 | Zerbe et al. |
| 6,231,957 B1 | 5/2001 | Zerbe et al. |
| 6,284,264 B1 | 9/2001 | Zerbe et al. |
| 6,375,963 B1 | 4/2002 | Repka et al. |
| 6,800,329 B2 | 10/2004 | Horstmann et al. |
| 6,824,829 B2 | 11/2004 | Berry et al. |
| 7,005,142 B2 | 2/2006 | Leon |
| 7,357,891 B2 * | 4/2008 | Yang et al. ................ 264/211.12 |
| 7,579,019 B2 | 8/2009 | Tapolsky et al. |
| 2001/0006677 A1 | 7/2001 | McGinity et al. |
| 2001/0022964 A1 | 9/2001 | Leung et al. |
| 2001/0046511 A1 | 11/2001 | Zerbe et al. |
| 2002/0127254 A1 | 9/2002 | Fotinos et al. |
| 2003/0107149 A1 | 6/2003 | Yang et al. |
| 2004/0096569 A1 | 5/2004 | Barkalow et al. |
| 2004/0191302 A1 | 9/2004 | Davidson |
| 2005/0048102 A1 | 3/2005 | Tapolsky et al. |
| 2006/0110610 A1 | 9/2006 | Davidson et al. |
| 2007/0087036 A1 | 4/2007 | Durschlag et al. |
| 2007/0148097 A1 | 6/2007 | Finn et al. |

FOREIGN PATENT DOCUMENTS

| | | |
|---|---|---|
| EP | 0273069 A1 | 7/1988 |
| EP | 0381194 | 8/1990 |
| EP | 0514691 A2 | 11/1992 |
| EP | 0598606 B1 | 6/1999 |
| EP | 1110546 | 6/2001 |
| GB | 1510999 | 5/1978 |
| JP | 62126950 | 6/1987 |
| JP | 02265444 | 10/1990 |
| JP | 05147140 | 6/1993 |
| JP | 07322812 | 12/1995 |
| JP | 2001279100 | 10/2001 |
| WO | WO 92/15289 A1 | 9/1992 |
| WO | WO 95/05416 A2 | 2/1995 |
| WO | WO 95/18046 A1 | 7/1995 |
| WO | WO 00/18365 | 4/2000 |
| WO | WO0018365 * | 4/2000 |
| WO | WO0018365 A2 | 4/2000 |
| WO | WO 00/42992 | 7/2000 |
| WO | WO 01/70194 A1 | 9/2001 |
| WO | WO 01/91721 A1 | 12/2001 |
| WO | WO03030882 A1 | 4/2003 |
| WO | WO03000882 A1 | 4/2003 |
| WO | WO03030881 A1 | 4/2003 |
| WO | WO03030883 A1 | 4/2003 |
| WO | WO2008011194 A2 | 1/2008 |

* cited by examiner

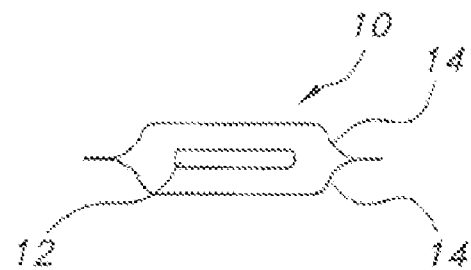
FIG. 1
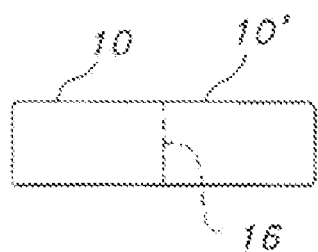
FIG. 2
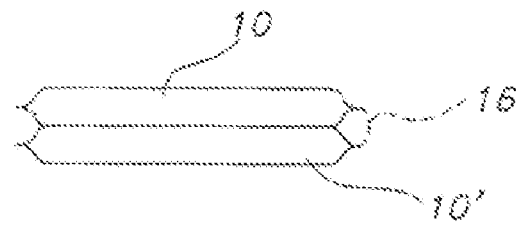
FIG. 3
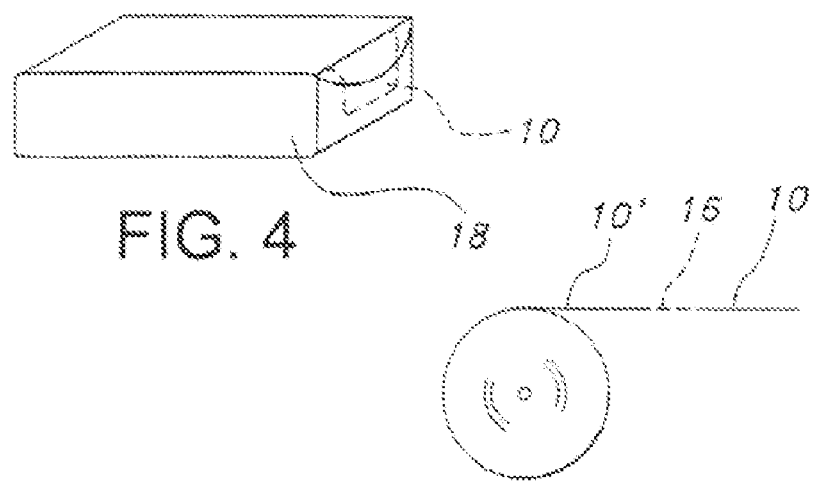
FIG. 4
FIG. 5

EDIBLE WATER-SOLUBLE FILM CONTAINING A FOAM REDUCING FLAVORING AGENT

CROSS-REFERENCE TO RELATED APPLICATIONS

This application claims priority to U.S. Provisional Application Ser. No. 60/846,064 filed on Sep. 20, 2006, the contents of which are incorporated by reference.

FIELD OF THE INVENTION

This invention relates to edible water-soluble films and, more specifically, to edible water-soluble films that include alternatives to traditional anti-foaming or defoaming agents.

BACKGROUND OF THE RELATED TECHNOLOGY

Films may be used as a delivery system to carry active ingredients such as drugs, pharmaceuticals, and the like. However, historically films and the process of making drug deliver systems therefrom have suffered from a number of unfavorable characteristics that have not allowed them to be used in practice.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water soluble polymers, surfactants, flavors, sweeteners, plastickers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

Examination of films made in accordance with the process disclosed in Fuchs, however, reveals that such films suffer from the aggregation or conglomeration of particles, i.e., self-aggregation, making them inherently non-uniform. This result can be attributed to Fuchs' process parameters, which although not disclosed likely include the use of relatively long drying times, thereby facilitating intermolecular attractive forces, convection forces, air flow and the like to form such agglomeration.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent standards of governmental or regulatory agencies, such as the U.S. Federal Drug Administration ("FDA"), relating to the variation of active in dosage forms. Currently, as required by various world regulatory authorities, dosage forms may not vary more than 10% in the amount of active present. When applied to dosage units based on films, this virtually mandates that uniformity in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area. Schmidt abandoned the idea that a mono-layer film, such as described by Fuchs, may provide an accurate dosage form and instead attempted to solve this problem by forming a multi-layered film. Moreover, his process is a multi-step process that adds expense and complexity and is not practical for commercial use.

Other U.S. Patents directly addressed the problems of particle self-aggregation and non-uniformity inherent in conventional film forming techniques. In one attempt to overcome non-uniformity, U.S. Pat. No. 5,629,003 to Horstmann et al. and U.S. Pat. No. 5,948,430 to Zerbe et al. incorporated additional ingredients, i.e. gel formers and polyhydric alcohols respectively, to increase the viscosity of the film prior to drying in an effort to reduce aggregation of the components in the film. These methods have the disadvantage of requiring additional components, which translates to additional cost and manufacturing steps. Furthermore, both methods employ the use the conventional time-consuming drying methods such as a high-temperature air-bath using a drying oven, drying tunnel, vacuum drier, or other such drying equipment. The long length of drying time aids in promoting the aggregation of the active and other adjuvant, notwithstanding the use of viscosity modifiers. Such processes also run the risk of exposing the active, i.e., a drug, or vitamin C, or other components to prolonged exposure to moisture and elevated temperatures, which may render it ineffective or even harmful.

In addition to the concerns associated with degradation of an active during extended exposure to moisture, the conventional drying methods themselves are unable to provide uniform films. The length of heat exposure during conventional processing, often referred to as the "heat history", and the manner in which such heat is applied, have a direct effect on the formation and morphology of the resultant film product. Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying. Thus, observation of relatively thick films made from such conventional processing shows a non-uniform structure caused by convection and intermolecular forces and requires greater than 10% moisture to remain flexible. The amount of free moisture can often interfere over time with the drug leading to potency issues and therefore inconsistency in the final product.

Conventional drying methods generally include the use of forced hot air using a drying oven, drying tunnel, and the like. The difficulty in achieving a uniform film is directly related to the rheological properties and the process of water evaporation in the film-forming composition. When the surface of an aqueous polymer solution is contacted with a high temperature air current, such as a film-forming composition passing through a hot air oven, the surface water is immediately evaporated forming a polymer film or skin on the surface. This seals the remainder of the aqueous film-forming composition beneath the surface, forming a barrier through which the remaining water must force itself as if is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repealed destruction and reformation of the film surface is observed as a "ripple effect" which produces an uneven, and therefore non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film suitable for commercialization and regulatory approval. Air can be trapped in the composition during the mixing process or later during the film making process, which can leave voids in the film product as the moisture evaporates during the drying stage. The film frequently collapse around the voids resulting in an uneven film surface and therefore, non-uniformity of the final film product. Uniformity is still affected even if the voids in the film caused by air bubbles do not collapse. This situation also provides a non-uniform film in that the spaces, which are not uniformly distributed, are occupying area that would otherwise be occupied by the film composition. None of the above-mentioned patents either addresses or proposes a solution to the problems caused by air that has been introduced to the film.

Another goal in the manufacture of films to be used as a delivery system is the minimization of materials or components. Because the films are often very thin, it can be a challenge to incorporate a high load of active ingredient while maintaining the film's uniformity.

Another factor affecting the uniformity of films is the prevention of air bubbles in the film. Anti-foaming and/or defoaming components may be used to aid in the removal of air, such as entrapped air, from the film-forming compositions. Such entrapped air may lead to non-uniform films.

Anti-foaming/defoaming components typically have a low hydrophilic/lipophilic balance. In other words, they are often oily. One example of a conventional anti-foaming/defoaming component is simethicone. Simethicone is a mixture of fully methylated linear siloxane polymers containing repeating units of polydimethylsiloxane which is stabilized with trimethylsiloxy end-blocking unites, and silicon dioxide, it usually contains 90.5-99% polymethylsiloxane and 4-7% silicon dioxide. The mixture is a gray, translucent, viscous fluid which is insoluble in water. When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be dissipated. Simethicone acts as a anti-foaming/defoaming component by both lowering the surface energy of any air bubbles trapped inside the aqueous solution, as well as lowering the surface tension of the aqueous solution.

However, the anti-foaming/defoaming components themselves can sometimes also lead to non-uniform films. Because of the nature of anti-foaming/defoaming components, they can cause mottling of the product, i.e., clear spots in the translucent film.

Therefore, there is a need for methods and compositions for film products, which use a minimal number of materials or components, and which provide a substantially non-self-aggregating uniform heterogeneity throughout the area of the film.

SUMMARY OF THE INVENTION

In accordance with the present invention, an edible water-soluble film is provided. The edible water-soluble film includes at least one water-soluble polymer, and a foam reducing flavoring agent, wherein the film is free of added anti-foaming or defoaming agents.

In a preferred embodiment, the foam reducing flavoring agent is present in amount of about 0.1% to about 20% by weight of the film. In another preferred embodiment, the foam reducing flavoring agent is present in amount of about 0.5% to about 15% by weight of the film.

In a preferred embodiment, the foam reducing flavoring agent is fruit or aromatic or bark based. In another preferred embodiment, the foam reducing flavoring agent is selected from the group consisting of menthol cherry menthol, cinnamint, spearmint, peppermint, orange flavor, natural raspberry and combinations thereof. In another preferred embodiment, the foam reducing flavoring agent includes 8 to 12 carbon atoms, at least one terminal dimethyl group, and a non-terminal OH group.

In another preferred embodiment, the water-soluble polymer includes a polymer selected from the group consisting of a cellulosic material, polyethylene oxide, a polysaccharide, a gum, a protein, a starch, a glucan, and combinations thereof. In another embodiment, the water-soluble polymer is selected from the group consisting of carboxymethyl cellulose, hydroxyl methyl cellulose, hydroxyethyl cellulose, hydroxypropyl cellulose hydroxypropylmethyl cellulose, polyethylene oxide, and combinations thereof. In another embodiment, the water-soluble polymer is selected from the group consisting of gum arabic, xanthan gum, tragacanth, acacia, carageenan, guar gum, locust bean gum, pectin, alginates and combinations thereof. In another embodiment, the water-soluble polymer is selected from the group consisting of polydextrose, dextrin, dextran and combinations thereof.

The film can also include an active component. In one embodiment, the active component is selected from the group consisting of cosmetic agents, pharmaceutical agents, bioactive agents and combinations thereof. In another embodiment, the active component is present in amounts of up to about 60% by weight of the film.

The film can further include one or more agents selected from the group consisting of taste-masking agents, plasticizing agents, surfactants, emulsifying agents, thickening agents, binding agents, cooling agents, saliva-stimulating agents, sweetening agents, antimicrobial agents and combinations thereof.

In another aspect of the invention, a method of preparing a substantially uniform film composition is provided. The method includes:
 a) preparing a film-forming composition comprising a water-soluble polymer, a foam reducing flavoring agent, and a polar solvent;
 b) mixing said film-forming composition under vacuum;
 c) casting said film-forming composition; and
 d) removing said polar solvent through a controlled drying process.

The edible water-soluble film of the invention provides a substantially non-self-aggregating uniform heterogeneity throughout the area of the film. By utilizing a foam reducing flavoring agent, instead of a conventional foam reducing agent, the film of the present invention has a uniform appearance, without mottling. Also, by avoiding the addition of a conventional foam reducing agent, the film of the present invention can accommodate added active ingredient.

BRIEF DESCRIPTION OF THE DRAWINGS

FIG. 1 shows a side view of a package containing a unit dosage film of the present invention.

FIG. 2 shows a top view of two adjacently coupled packages containing individual unit dosage forms of the present invention, separated by a tearable perforation.

FIG. 3 shows a side view of the adjacently coupled packages of FIG. 2 arranged in a stacked configuration.

FIG. 4 shows a perspective view of a dispenser for dispensing the packaged unit dosage forms, dispenser containing the packaged unit dosage forms in a stacked configuration.

FIG. 5 is a schematic view of a roll of coupled unit dose packages of the present invention.

DETAILED DESCRIPTION OF THE INVENTION

Figure 6:
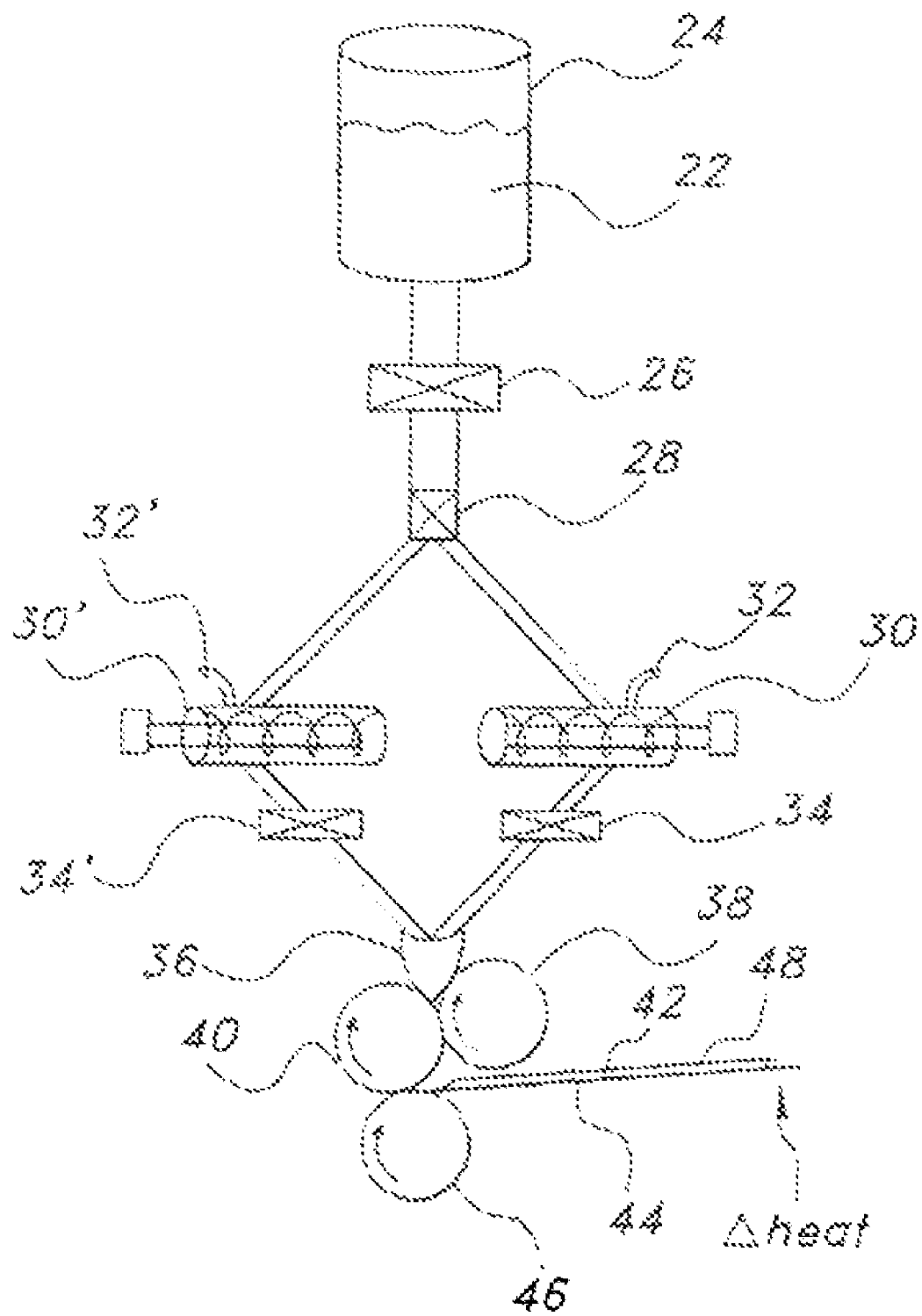
FIG. 6 is a schematic view of an apparatus suitable for preparation of a pre-mix, addition of an active, and subsequent formation of the film.

The present invention provides an edible water-soluble film. The film includes at least one soluble polymer. In addition, unlike conventional films, the film of the invention is free of added anti-foaming or defoaming agents. Instead, the present invention utilizes a foam reducing flavoring agent to provide a non-self-aggregating uniform film.

For the purposes of the present invention the term non-self-aggregating uniform heterogeneity refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films.

Furthermore, the films of the present invention have a substantially uniform thickness, which is also not provided by the use of conventional drying methods used for drying water-based polymer systems. The absence of a uniform thickness detrimentally affects uniformity of component distribution throughout the area of a given film.

The film products of the present invention are produced by a combination of a properly selected polymer and a polar solvent, optionally including an active ingredient as well as other fillers known in the art. These films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. No. 4,631,837 to Magoon ("Magoon"), herein incorporated by reference, as well as hot air impingement across the bottom substrate and bottom heating plates. Another drying technique for obtaining the films of the present invention is controlled radiation drying, in the absence of uncontrolled air currents, such as infrared and radio frequency radiation (i.e. microwaves).

The objective of the drying process is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed.

These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow.

Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents.

Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account by the present invention for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_1$) and increase the viscosity of the liquid phase ($\mu$). For an isolated particle, Stokes law relates the terminal settling velocity (Vo) of a rigid spherical body of radius (r) in a viscous fluid, as follows:

$$V_o = (2gr^F)(\rho_p - \rho_1)/9\mu$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analyses has shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as:

$$v/V_o = 1/(1+\kappa\phi)$$

where $\kappa$ = a constant and $\phi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o = 1 + 2.5\phi$$

where $\mu_o$ is the viscosity of the continuous phase and $\phi$ is the solids volume fraction. At higher volume fractions, the viscosity of the dispersion can be expressed as $$\mu/\mu_o = 1 + 2.5\phi + C_1\phi^2 + C_2\phi^3 + \ldots$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity and can impart stability depending on the type of hydrocolloid, its concentration and the particle composition, geometry, size, and volume fraction. The particle size distribution of the dispersed phase needs to be controlled by selecting the smallest realistic particle size in the high viscosity medium, i.e., <500 μm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max} = 3V\mu/2r$$

For pseudoplastic fluids, the viscosity in tins shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time period, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt. %, in a viscoelastic fluid matrix with acceptable viscosity values throughout a broad shear rate range. During mixing, pumping, and film casting, shear rates in the range of 10-$10^5$ sec.$^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, structural recovery will influence the quality of the film. As an illustrative example, the leveling of shear-thinning pseudoplastic fluids has been derived as $$\alpha^{(n-1/n)} = \alpha_o^{(n-1/n)} - ((n-1)/(2n-1))(\tau/K)^{1/n}(2\pi/\lambda)^{(3+n)/n}h_{(2n+1)/n_t}$$

where $\alpha$ is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present invention have a very rapid structural recovery, i.e. as the film is formed during processing, it doesn't fall apart or become discontinuous in its structure and compositional uniformity. Such very rapid structural recovery retards particle settling and sedimentation. Moreover, the films or film-forming compositions of the present invention are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of particle size and particle shape are further considerations. Desirably, the size of the particulate a particle size of 150 microns or less, for example 100 microns or less. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles.

In addition to adding a foam reducing flavoring agent, as further discussed below, a number of techniques may be employed in the mixing stage to prevent bubble inclusions in the final film. To provide a composition mixture with substantially no air bubble formation in the final product, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients such as drug particles. The actives are added to smaller mixes of the masterbatch just prior to casting. Thus, the masterbatch pre-mix can be allowed to stand for a longer time without concern for instability in drug or other ingredients.

When the matrix is formed including the film-forming polymer and polar solvent in addition to any additives and the active ingredient, this may be done in a number of steps. For example, the ingredients may all be added together or a pre-mix may be prepared. The advantage of a pre-mix is that all ingredients except for the active may be combined in advance, with the active added just prior to formation of the film. This is especially important for actives that may degrade with prolonged exposure to water, air or another polar solvent.

FIG. 6 shows an apparatus 20 suitable for the preparation of a pre-mix, addition of an active and subsequent formation of a film. The pre-mix or master batch 22, which includes the film-forming polymer, polar solvent, and any other additives except a drug active is added to the master batch feed tank 24. The components for pre-mix or master batch 22 are desirably formed in a mixer (not shown) prior to their addition into the master batch feed tank 24. Then a pre-determined amount of the master batch is controllably fed via a first metering pump 26 and control valve 28 to either or both of the first and second mixers, 30, 30'. The present invention, however, is not limited to the use of two mixers, 30, 30', and any number of mixers may suitably be used. Moreover, the present invention is not limited to any particular sequencing of the mixers 30, 30', such as parallel sequencing as depicted in FIG. 6, and other sequencing or arrangements of mixers, such as series or combination, of parallel and series, may suitably be used. The required amount of the drug or other ingredient, such as a flavor, is added to the desired mixer through an opening, 32, 32', in each of the mixers, 30, 30'. Desirably, the residence time of the pre-mix or master batch 22 is minimized in the mixers 30, 30'. While complete dispersion of the drug into the pre-mix or master batch 22 is desirable, excessive residence times may result in leaching or dissolving of the drug, especially in the case for a soluble drug. Thus, the mixers 30, 30' are often smaller, i.e. lower residence times, as compared to the primary mixers (not shown) used in forming the pre-mix or master batch 22. After the drug has been blended with the master batch pre-mix for a sufficient time to provide a uniform matrix, a specific amount of the uniform matrix is then fed to the pan 36 through tire second metering pumps, 34, 34'. The metering roller 38 determines the thickness of the film 42 and applies it to the application roller. The film 42 is finally formed on the substrate 44 and carried away via the support roller 46.

While the proper viscosity uniformity in mixture and stable suspension of particles, and casting method are important in the initial steps of forming the composition and film to promote uniformity, the method of drying the wet film is also important. Although these parameters and properties assist uniformity initially, a controlled rapid drying process ensures that the uniformity will be maintained until the film is dry.

The wet film is then dried using controlled bottom drying or controlled microwave drying, desirably in the absence of external air currents or heat on the top (exposed) surface of the film 48 as described herein. Controlled bottom drying or controlled microwave drying advantageously allows for vapor release from the film without the disadvantages of the prior art. Conventional convection air drying from the top is not employed because it initiates drying at the top uppermost portion of the film, thereby forming a barrier against fluid flow, such as the evaporative vapors, and thermal flow, such as the thermal energy for drying. Such dried upper portions serve as a barrier to further vapor release as the portions beneath are dried, which results in non-uniform films. As previously mentioned some top air flow can be used to aid the drying of the films of the present invention, but it must not create a condition that would cause particle movement or a rippling effect in the film, both of which would result in non-uniformity. If top air is employed, it is balanced with the bottom air drying to avoid non-uniformity and prevent film lift-up on the carrier belt. A balance top and bottom air flow may be suitable where the bottom air flow functions as the major source of drying and the top air How is the minor source of drying. The advantage of some top air flow is to move the exiting vapors away from the film thereby aiding in the overall drying process. The use of any top air flow or top drying, however, must be balanced by a number of factors including, but not limited, to rheological properties of the composition and mechanical aspects of the processing. Any top fluid flow, such as air, also must not overcome the inherent viscosity of the film-forming composition. In other words, the top air flow cannot break, distort or otherwise physically disturb the surface of the composition. Moreover, air velocities are desirably below the yield values of the film, i.e., below any force level that can move the liquids in the film-forming compositions. For thin or low viscosity compositions, low air velocity must be used. For thick or high viscosity compositions, higher air velocities may be used. Furthermore, air velocities are desirable low so as to avoid any lifting or other movement of the film formed from the compositions.

Moreover, the films of the present invention may contain particles that are sensitive to temperature, such as flavors, which may be volatile, or drugs, which may have a low degradation temperature. In such cases, the drying temperature may be decreased while increasing the drying time to adequately dry the uniform films of the present invention. Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

During film preparation, it may be desirable to dry films at high temperatures. High heat drying produces uniform films, and leads to greater efficiencies in film production. Films containing sensitive active components, however, may face degradation problems at high temperatures. Degradation is the "decomposition of a compound . . . exhibiting well-defined intermediate products." The American Heritage Dictionary of the English Language (4$^{th}$ ed. 2000). Degradation of an active component is typically undesirable as it may cause instability, inactivity, and/or decreased potency of the active component. For instance, if the active component is a drug or bioactive material, this may adversely affect the safety or efficacy of the final pharmaceutical product. Additionally, highly volatile materials will tend to be quickly released from this film upon exposure to conventional drying methods.

Degradation of an active component may occur through a variety of processes, such as, hydrolysis, oxidation, and light degradation, depending upon the particular active component. Moreover, temperature has a significant effect on the rate of such reactions. The rate of degradation typically doubles for every 10° C. increase in temperature. Therefore, it is commonly understood that exposing an active component to high temperatures will initiate and/or accelerate undesirable degradation reactions.

Proteins are one category of useful active agents that may degrade, denature, or otherwise become inactive when they are exposed to high temperatures for extended periods of time. Proteins serve a variety of functions in the body such as enzymes, structural elements, hormones and immunoglobulins. Examples of proteins include enzymes such as pancreatin, trypsin, pancrelipase, chymotrypsin, hyaluronidase, sutilains, streptokinaw, urokinase, altiplase, papain, bromelainsdiastase, structural elements such as collagen, elastin and albumin, hormones such as thyroliberin, gonadoliberin, adrenocorticottropin, corticotrophin, cosyntropin, sometrem, somatropion, prolactin, thyrotropin, somatostatin, vasopressin, felypressin, lypressin, insulin, glucagons, gastrin, pentagastrin, secretin, cholecystokinin-pancreozymin, and immunomodulatory which may include polysaccharides in addition to glycoproteins including cytokines which are useful for the inhibition and prevention of malignant cell growth such as tumor growth. A suitable method for the production of some useful glycoproteins is disclosed in U.S. Pat. No. 6,281, 337 to Cannon-Carlson, et al., which in incorporated herein in its entirety.

Peptides are another category of useful active agents that have the potential to become inactive when exposed to high temperatures for long periods of time.

Temperatures that approach 100° C. will generally cause degradation of proteins, certain peptides, as well as nucleic acids. For example, some glycoproteins will degrade if exposed to a temperature of 70° C. for thirty minutes. Proteins from bovine extract are also known to degrade at such low temperatures. DNA also begins to denature at this temperature.

Applicants have discovered, however, that the films of the present invention may be exposed to high temperatures during the drying process without concern for degradation, loss of activity, or excessive evaporation due to the inventive process for film preparation and forming. In particular, the films may be exposed to temperatures that would typically lead to degradation, denaturization, or inactivity of the active component, without causing such problems. According to the present invention, the manner of drying may be controlled to prevent deleterious levels of heat from reaching the active component.

As discussed herein, the flowable mixture is prepared to be uniform in content in accordance with the teachings of the present invention. Uniformity must be maintained as the flowable mass was formed into a film and dried. During the drying process of the present invention, several factors produce uniformity within the film while maintaining the active component at a safe temperature, i.e., below its degradation temperature. First, the films of the present invention have an extremely short heat history, usually only on the order of minutes, so that total temperature exposure is minimized to the extent possible. The films are controllably dried to prevent aggregation and migration of components, as well as preventing heat build up within. Desirably, the films are dried from the bottom. Controlled bottom drying, as described herein, prevents the formation of a polymer film, or skin, on the top surface of the film. As heat is conducted from the film bottom upward, liquid carrier, e.g., water, rises to the film surface. The absence of a surface skin permits rapid evaporation of the liquid carrier as the temperature increases, and thus, concurrent evaporative cooling of the film. Due to the short heat exposure and evaporative cooling, the film components such as drag or volatile actives remain unaffected by high temperatures. In contrast, skinning on the top surface traps liquid carrier molecules of increased energy within the film, thereby causing the temperature within the film to rise and exposing active components to high, potentially deleterious temperatures.

Second, thermal mixing occurs within the film due to bottom heating and absence of surface skinning. Thermal mixing occurs via convection currents in the film. As heat is applied to the bottom of the film, the liquid near the bottom increases in temperature, expands, and becomes less dense. As such, this hotter liquid rises and cooler liquid takes its place. While rising, the hotter liquid mixes with the cooler liquid and shares thermal energy with it, i.e., transfers heat. As the cycle repeats, thermal energy is spread throughout the film.

Robust thermal mixing achieved by the controlled drying process of the present invention produces uniform heat diffusion throughout the film. In the absence of such thermal mixing, "hot spots" may develop. Pockets of heat in the film result in the formation of particle aggregates or danger areas within the film and subsequent non-uniformity. The formation of such aggregates or agglomerations is undesirable because it leads to non-uniform films in which the active may be randomly distributed. Such uneven distribution may lead to large differences in the amount of active per film, which is problematic from a safety and efficacy perspective.

Furthermore, thermal mixing helps to maintain a lower overall temperature inside the film. Although the film surfaces may be exposed to a temperature above that at which the active component degrades, the film interior may not reach this temperature. Due to this temperature differential, the active does not degrade.

For instance, the films of the present invention desirably are dried for 10 minutes or less. Drying the films at 80° C. for 10 minutes produces a temperature differential of about 5° C. This means that after 10 minutes of drying, the temperature of the inside of the film is 5° C. less than the outside exposure temperature. In many cases, however, drying times of less than 10 minutes are sufficient, such as 4 to 6 minutes. Drying for 4 minutes may be accompanied by a temperature differential of about 30° C., and drying for 6 minutes may be accompanied by a differential of about 25° C. Due to such large temperature differentials, the films may be dried at efficient, high temperatures without causing heat sensitive actives to degrade.

Figure 7:
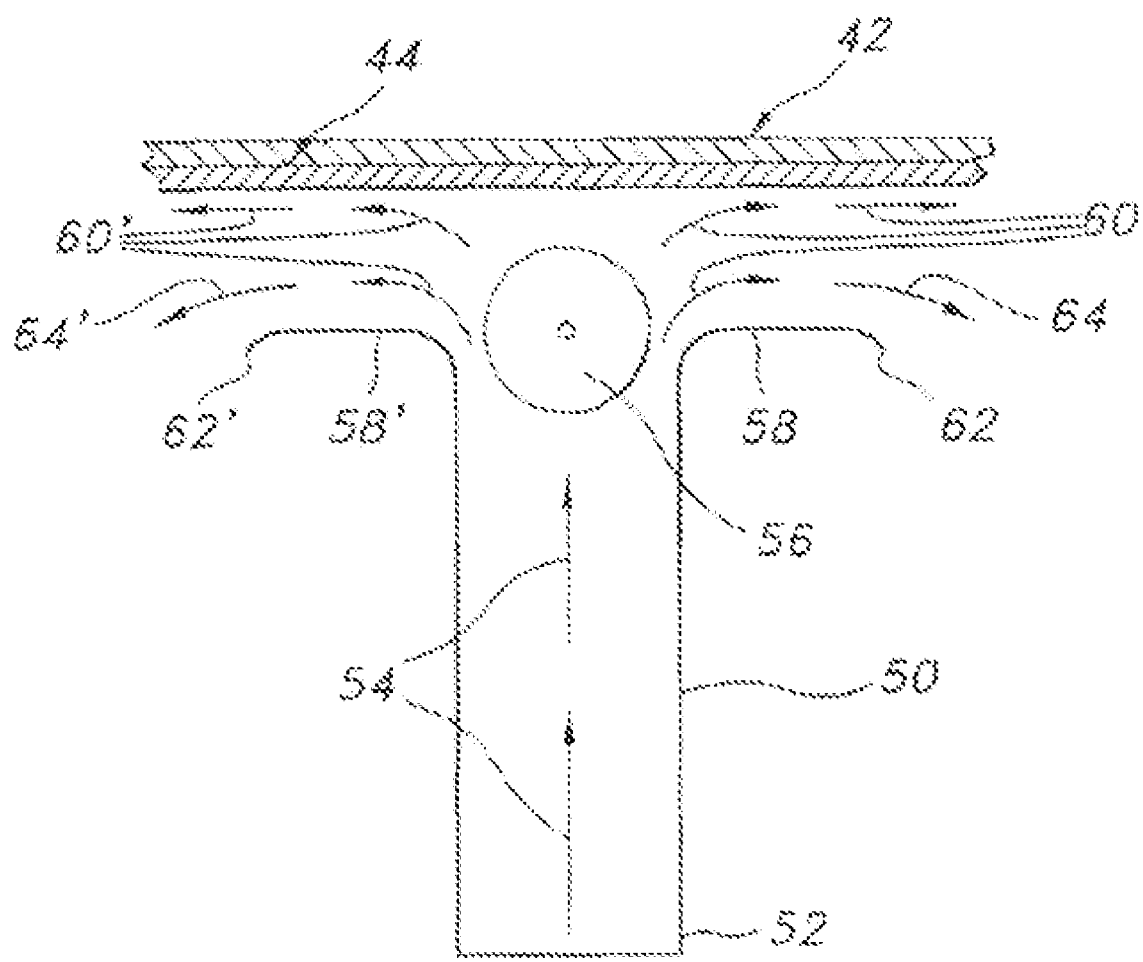
FIG. 7 is a schematic view of an apparatus suitable for drying the films of the present invention.
Figure 8:
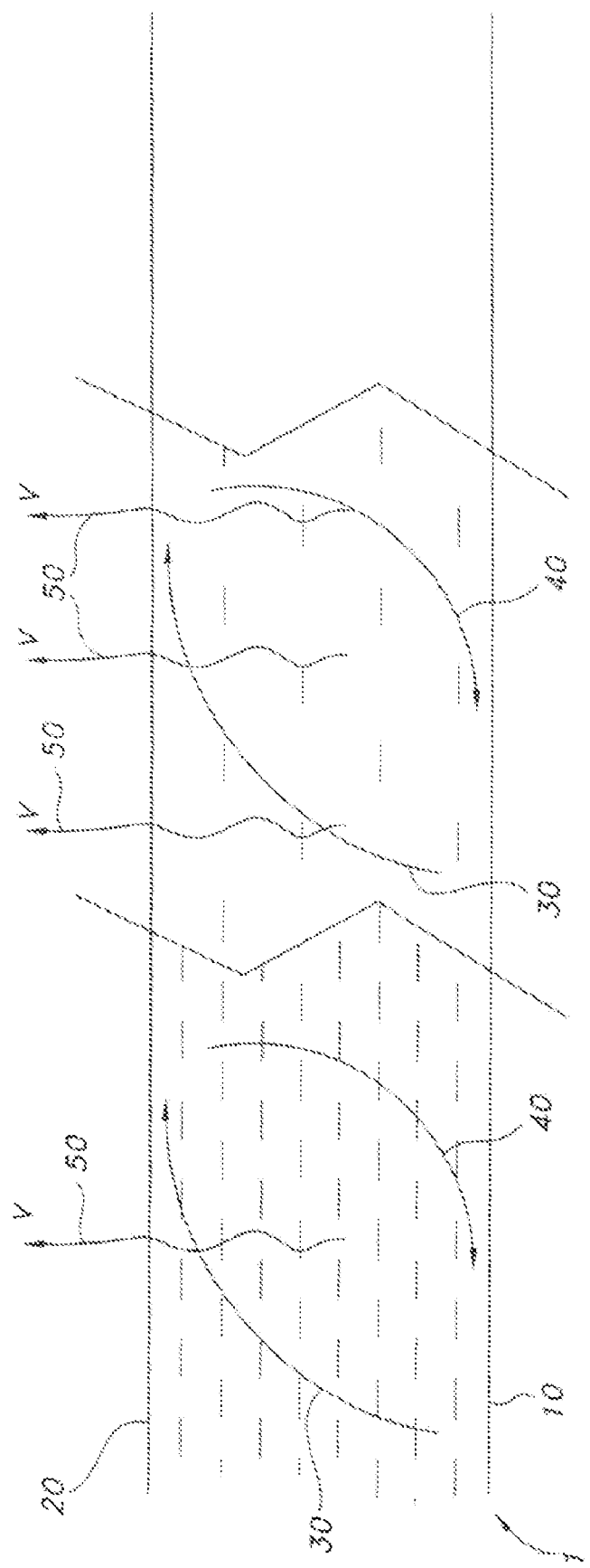
FIG. 8 is a sequential representation of the drying process of the present invention.

FIG. 8 is a sequential representation of the drying process of the present invention. After mechanical mixing, the film may be placed on a conveyor for continued thermal mixing during the drying process. At the outset of the drying process, depicted in Section A, the film 1 preferably is heated from the bottom 10 as it is travels via conveyor (not shown). Heat may be supplied to the film by a heating mechanism, such as, but not limited to, the dryer depicted in FIG. 7. As the film is heated, the liquid carrier, or volatile ("V"), begins to evaporate, as shown by upward arrow 50. Thermal mixing also initiates as hotter liquid, depicted by arrow 30, rises and cooler liquid, depicted by arrow 40, takes its place. Because no skin forms on the top surface 20 of the film 1, as shown in Section B the volatile liquid continues to evaporate 50 and thermal mixing 30/40 continues to distribute thermal energy throughout the film. Once a sufficient amount of the volatile liquid has evaporated, thermal mixing has produced uniform heat diffusion throughout the film 1. The resulting dried film 1 is a visco-elastic solid, as depicted in Section C. The components desirably are locked into a uniform distribution throughout the film. Although minor amounts of liquid carrier, i.e., water, may remain subsequent to formation of the visco-elastic, the film may be dried further without movement of the particles, if desired.

Furthermore, particles or particulates may be added to the film-forming composition or matrix after the composition or matrix is cast into a film. For example, particles may be added to the film 42 prior to the drying of the film 42. Particles may be controllably metered to the film and disposed onto the film through a suitable technique, such as through the use of a doctor blade (not shown) which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The particles may be any useful organoleptic agent, cosmetic agent, pharmaceutical agent, or combinations thereof. Desirably, the pharmaceutical agent is a taste-masked or a controlled-release pharmaceutical agent. Useful organoleptic agents include flavors and sweeteners. Useful cosmetic agents include breath freshening or decongestant agents.

Although the inventive process is not limited to any particular apparatus for the above-described desirable drying, one particular useful drying apparatus 50 is depicted in FIG. 7. Drying apparatus 50 is a nozzle arrangement for directing hot fluid, such as but not limited to hot air, towards the bottom of the film 42 which is disposed on substrate 44. Hot air enters the entrance end 52 of the drying apparatus and travels vertically upward, as depicted by vectors 54, towards air deflector 56. The air deflector 56 redirects the air movement to minimize upward force on the film 42. As depicted in FIG. 7, the air is tangentially directed, as indicated by vectors 60 and 60', as the air passes by air deflector 56 and enters and travels through chamber portions 58 and 58' of the drying apparatus 50. With the hot air flow being substantially tangential to the film 42, lifting of the film as it is being dried is thereby minimized. While the air deflector 56 is depicted as a roller, other devices and geometries for deflecting air or hot fluid may suitable be used. Furthermore, the exit ends 62 and 62' of the drying apparatus 50 are flared downwardly. Such downward flaring provides a downward force or downward velocity vector, as indicated by vectors 64 and 64', which tend to provide a pulling or drag effect of the film 42 to prevent lifting of the film 42. Lifting of the film 42 may not only result in non-uniformity in the film or otherwise, but may also result in non-controlled processing of the film 42 as the film 42 and/or substrate 44 lift away from the processing equipment.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness.

The film products are generally formed by combining a properly selected polymer and polar solvent, as well as any active ingredient or filler as desired. Desirably, the solvent content of the combination is at least about 30% by weight of the total combination. The matrix formed by this combination is formed into a film, desirably by roll coating, and then dried, desirably by a rapid and controlled drying process to maintain tire uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

Consideration of the above discussed parameters, such as but not limited to rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product having no more than a 10% variance of a pharmaceutical and/or cosmetic active per unit area. In other words, the uniformity of the present invention is determined by the presence of no more than a 10% by weight of pharmaceutical and/or cosmetic variance throughout the matrix. Desirably, the variance is less than 5% by weight, less than 2% by weight, less than 1% by weight, or less than 0.5% by weight.

Fine-Forming Polymers

The film product of the present invention includes a water soluble polymer composition. The films include at least one water soluble polymer and may include other hydrophilic materials. The films may also include water swellable or water insoluble polymers, if desired.

In some embodiments, the water soluble polymer composition includes a hydrophilic material selected from the following: a saccharide-based polymer, a non-saccharide-based polymer, a sugar alcohol and combinations thereof.

In some embodiments, the self-supporting film includes a saccharide-based polymer, which is water soluble. For example, the saccharide-based polymer may be cellulose or a cellulose derivative. Specific examples of useful saccharide-based, water soluble polymers include, but are not limited to, polydextrose, pullulan, hydroxypropylmethyl cellulose (HPMC), hydroxyethyl cellulose (HPC), hydroxypropyl cellulose, carboxymethyl cellulose, sodium aginate, xanthan gum, tragancanth gum, guar gum, acacia gum, arabic gum, starch, gelatin, and combinations thereof.

In some preferred embodiments, the saccharide-based polymer may be at least one cellulosic polymer, polydextrose, or combinations thereof.

The film may also include non-saccharide-based, water soluble or water insoluble polymers. Examples of non-saccharide based, water soluble polymers include polyethylene oxide, polyvinylpyrrolidone, polyvinyl alcohol, polyethylene glycol, polyacrylic acid, methylmethacrylate copolymer, carboxyvinyl copolymers, and combinations thereof.

In some embodiments, the water soluble polymer composition includes a sugar alcohol. The sugar alcohol may be selected from, but is not limited to, one of the following: erythritol, sorbitol and xylitol.

Specific examples of useful water insoluble polymers include, but are not limited to, ethyl cellulose, hydroxypropyl ethyl cellulose, cellulose acetate phthalate, hydroxypropyl methyl cellulose phthalate and combinations thereof. In some embodiments, the water soluble polymer composition includes polyethylene oxide, alone or in combination with other hydrophilic materials.

In some embodiments, the water soluble polymer composition includes a combination of polyethylene oxide and polyvinylpyrrolidone. In other embodiments, the water soluble polymer composition includes a combination of polyethylene oxide and polyvinyl alcohol.

In some other embodiments, the water soluble polymer composition includes polyethylene oxide in combination with a cellulosic polymer. For example, the water soluble polymer composition may include a combination of polyethylene oxide and carboxymethyl cellulose. In further embodiments, the water soluble polymer composition includes a combination of polyethylene oxide and hydroxypropyl cellulose. In still further embodiments, the water soluble polymer composition includes a combination of polyethylene oxide and hydroxy propylmethyl cellulose.

In other embodiments, the water soluble polymer composition includes polyethylene oxide in combination with a sugar or sugar alcohol. For example, the water soluble polymer composition may include a combination of polyethylene oxide and polydextrose. In other embodiments, the water soluble polymer composition includes a combination of polyethylene oxide and erythritol. In further embodiments, the water soluble polymer composition includes a combination of polyethylene oxide and sorbitol. In other embodiments, the water soluble polymer composition includes a combination of polyethylene oxide and xylitol.

In further embodiments, the water soluble polymer composition comprises a combination of polyethylene oxide, hydroxypropyl methyl cellulose and polydextrose.

As used herein, the phrase "water soluble polymer" and variants thereof refer to a polymer that is at least partially soluble in a fluid, such as water, and desirably fully or predominantly soluble in the fluid, or absorbs the fluid. In some embodiments, the film product of the present invention is substantially dissolvable when exposed to a fluid.

Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with fluids.

Other polymers useful for incorporation into the films of the present invention include biodegradable polymers, copolymers, block polymers and combinations thereof. Among the known useful polymers or polymer classes which meet the above criteria, are: poly(glycolic acid) (PGA), poly (lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxy acetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the active agent or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active agent in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active agent component, depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsions/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer and/or polydextrose achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1ing to about 200 mg. The hydrophilic cellulosic polymer and/or polydextrose ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC) and/or polydextrose.

Controlled Release Films

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, sublingual and vaginal applications. The films of the present invention are particularly useful where mucosal membranes or mucosal fluid is present due to their ability to readily wet and adhere to these areas.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

The actives employed in the present invention may be incorporated into the film compositions of the present invention in a controlled release form. For example, particles of drug may be coated with polymers such as ethyl cellulose or polymethacrylate, commercially available under brand names such as Aquacoat BCD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

The actives may be taste-masked prior to incorporation into the film composition, as set forth in co-pending PCT application titled, Uniform Films For Rapid Dissolve Dosage Form Incorporating Taste-Masking Compositions, WO/2003/030883, the entire disclosure of which is incorporated by reference herein.

Actives

When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

The active components that may be incorporated into the films of the present invention include, without limitation pharmaceutical and cosmetic actives, drugs, medicaments, antigens or allergens such as ragweed pollen, spores, microorganisms including bacteria, seeds, mouthwash components such as chlorates or chlorites, flavors, fragrances, enzymes, preservatives, sweetening agents, colorants, spices, vitamins and combinations thereof.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, antihistamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine and nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DMA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active ingredients for use in the present invention include anti-diarrheals such as immodium AD, antihistamines, anti-tussives, decongestants, vitamins, and breath fresheners. Suitable vitamins contemplated for use herein include any conventionally known vitamins, such as, but not limited to. Vitamins A, B, C and E. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®), anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and $Ca^H$-antagonists such as nifedipine (available as Procardia® and Adalal®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenergic) activities. Useful non-limiting drugs include sildenafil, such as Viagra®, tadalafils, such as Cialis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Botanicals, herbals and minerals also may be added to the film. Examples of botanicals include, without limitation: roots; barks; leaves; stems; flowers; fruits; tobacco; sunflower seeds; snuff; and combinations thereof.

An anti-oxidant may also be added to the film to prevent the degradation of an active, especially where the active is photosensitive.

The bioactive active substances employed in the present invention may include beneficial bacteria. More specifically, certain bacteria normally exist on the surface of the tongue and in the back of the throat. Such bacteria assist in the digestion of food by breaking down proteins found in the food. It may be desirable, therefore, to incorporate these bacteria into the oral film products of the present invention.

It also may be desirable to include actives for treating breath malodor and related oral care conditions, such as actives which are effective in suppressing microorganisms. Because breath malodor can be caused by the presence of anaerobic bacteria in the oral cavity, which generate volatile sulfur compounds, components that suppress such microorganisms may be desirable. Examples of such components include antimicrobials such as triclosan, chlorine dioxide, chlorates, and chlorites, among others. The use of chlorites, particularly sodium chlorite, in oral care compositions such as month rinses and toothpastes is taught in U.S. Pat. Nos. 6,251,372, 6,132,702, 6,077,502, and 6,696,047, all of which are incorporated herein by reference. Such components are incorporated, in amounts effective to treat malodor and related oral conditions.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame: dihydrochalcone compounds, glycyrrhizin; *Stevia Rebaudiana* (Stevioside); chloro derivatives of sucrose such as sucralose; sugar alcohols such as sorbitol mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

When the active is combined with the polymer in the solvent, the type of matrix that is formed depends on the solubilities of the active and the polymer. If the active and/or polymer are soluble in the selected solvent, this may form a solution. However, if the components are not soluble, the matrix may be classified as an emulsion, a colloid, or a suspension.

Dosages

The film products of the present invention are capable of accommodating a wide range of amounts of the active ingredient. The films are capable of providing an accurate dosage amount (determined by the size of the film and concentration of the active in the original polymer/water combination) regardless of whether the required dosage is high or extremely low. Therefore, depending on the type of active or pharmaceutical composition that is incorporated into the film, the active amount may be as high as about 300 mg, desirably up to about 150 mg or as low as the microgram range, or any amount therebetween.

The film products and methods of the present invention are well suited for high potency, low dosage drugs. This is accomplished through the high degree of uniformity of the films. Therefore, low dosage drugs, particularly more potent racemic mixtures of actives are desirable.

Foam Reducing Flavoring Agents

The film of the present invention also includes at least one foam reducing flavoring agent. A foam reducing flavoring agent as defined herein is a component that can act to both flavor the film and prevent and/or remove air, such as entrapped air, from the film-forming compositions.

The foam reducing flavoring agent is added instead of traditional anti-foaming or defoaming agents. Thus, the film of the present invention is free of added anti-foaming or defoaming agents.

The term "defoaming agents" is typically used to describe agents that reduce foam after it has already formed. The term "anti-foaming agents" is typically used to describe agents that prevent foam from forming during processing. For the purposes of this application, the terms are used interchangeably.

Conventional defoaming/anti-foaming agents are well known in the art. See, for example, McCutcheons Functional Materials, North American Edition/International Edition 2005 Annuals Volume 2, The Manufacturing Confectioner Publishing Co., "Defoamers," pp. 103-126 (2005), incorporated herein by reference. Many anti-foaming/defoaming agents are silicone or oil based. Simethicone is one well known anti-foaming/defoaming agent.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of a foam reducing flavoring agent into the film-forming composition either substantially reduces or eliminates the formation of air bubbles.

Flavor agents are typically added after mixing because mixing under vacuum can cause a decrease in the effect of certain flavors. However, since the foam reducing flavoring agent is used not only to flavor the film, but to also reduce foam, the foam reducing flavoring agent is preferably added before mixing the other ingredients in the film-forming solution. In this way the foam reducing flavoring agent can both prevent the formation of foam and help eliminate any foam that is formed, i.e., act as both an anti-foam agent and a defoaming agent.

In a preferred embodiment, the foam reducing flavoring agents are fruit or aromatic or hark based. For example, the foam reducing flavoring agent can be a mint-type flavor. Suitable mint-type flavors include menthol, cinnamint, spearmint, peppermint, and combinations thereof. Natural raspberry and orange flavor, such as Orange Burst flavor AN24334582 by Noville, are also a suitable foam reducing flavoring agents. The foam reducing flavoring agents can themselves be flavored. For example, instead of menthol, the foam reducing flavoring agent can be cherry menthol. Other variations are possible.

In a preferred embodiment, the foam reducing flavoring agent has 8 to 12 carbon atoms, more preferably 10 carbon atoms. In another preferred embodiment, the foam reducing flavoring agents contain at least one terminal dimethyl group and a non-terminal OH group. Without being bound by theory, it is believed that foam reducing flavoring agents with these chemical groups may have an effect in interacting with the air bubbles and releasing the air entrapped therein.

Foam reducing flavoring agents generally are present in any amount effective for the agent to both flavor the film and reduce the amount of foam produced when the film is being manufactured. For example, foam reducing flavoring agent may be present in an amount of at least 0.1%, preferably at least about 0.15%, more preferably at least about 0.5%, most preferably at least about 1.0% by weight of the film. In addition, the foam reducing flavoring agent may be present, for example, in an amount of at most 20%, preferably at most 1.5%, more preferably at most 10%, most preferably at most 5% by weight of the film.

Optional Components

A variety of other components and fillers may also be added to the films of the present invention. These may include, without limitation, surfactants; plasticizers which assist in compatibilizing the components within the mixture; polyalcohols; and thermo-setting gels such as pectin, carageenan, and gelatin, which help in maintaining the dispersion of components. Some surfactants can act as antifoam/deafoaming agents if they have a low hydrophile-lipophile balance ("HLB"), i.e., less than 5 HLB. Therefore, the surfactants that can be added to the films of the present invention are surfactants that are not intended for an antifoam/defoaming purpose, i.e., those surfactants that have an HLP greater than 5. Accordingly, "surfactant" as defined herein is intended to mean those surfactants not suitable as an antifoaming/defoaming agent.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. Such additives are known in the art (Again, as with surfactants, none of these additives are intended to include additives that act as an antifoaming/defoaming agent.) These additives may be added with the active ingredient(s).

Forming the Film

The films of the present invention must be formed into a sheet prior to drying. After the desired components are combined to form a multi-component matrix, including the polymer, water, and an active or other components as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

It may be particularly desirable to employ extrusion methods for forming film compositions containing PEO polymer components. These compositions contain PEO or PEO blends in the polymer component, and may be essentially free of added plasticizers, and/or surfactants, and polyalcohols. The compositions may be extruded as a sheet at processing temperatures of less than about 90° C. Extrusion may proceed by squeezing the film composition through rollers or a die to obtain a uniform matrix. The extruded film composition then is cooled by any mechanism known to those of ordinary skill in the art. For example, chill rollers, air cooling beds, or water cooling beds may be employed. The cooling step is particularly desirable for these film compositions because PEO tends to hold heat.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Prying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Desirably, substantially no air flow is present across the top of the film during its initial setting period, during which a solid, visco-elastic structure is formed. This can take place within the first few minutes, e.g. about the first 0.5 to about 4.0 minutes of the drying process. Controlling the drying in this manner, prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried is about 100° C. or less, desirably about 90° C. or less, and most desirably about 80° C. or less.

In some embodiments, the weight of the polar solvent is at least about 30% of the film before drying. In some other embodiments, the drying of the film reduces the weight percent of the polar solvent to about 10% or less. Preferably, the drying occurs within about 10 minutes or fewer.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

Another method of controlling the drying process involves a zone drying procedure. A zone drying apparatus may include a continuous belt drying tunnel having one or more drying zones located within. The conditions of each drying zone may vary, for example, temperature and humidity may be selectively chosen. It may be desirable to sequentially order the zones to provide a stepped up drying effect.

The speed of the zone drying conveyor desirably is continuous. Alternatively, the speed may be altered at a particular stage of the drying procedure to increase or decrease exposure of the film to the conditions of the desired zone. Whether continuous or modified, the zone drying dries the film without surface skinning.

Figure 9:
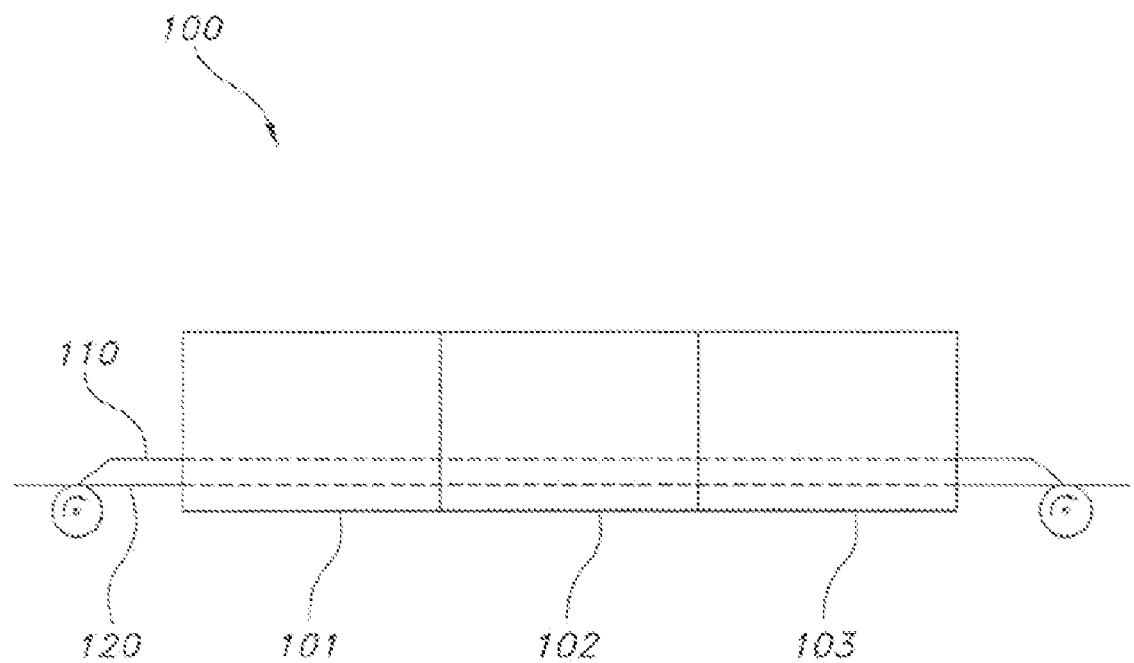
FIG. 9 is a schematic representation of a continuously-linked zone drying apparatus in accordance with the present invention.
Figure 10:
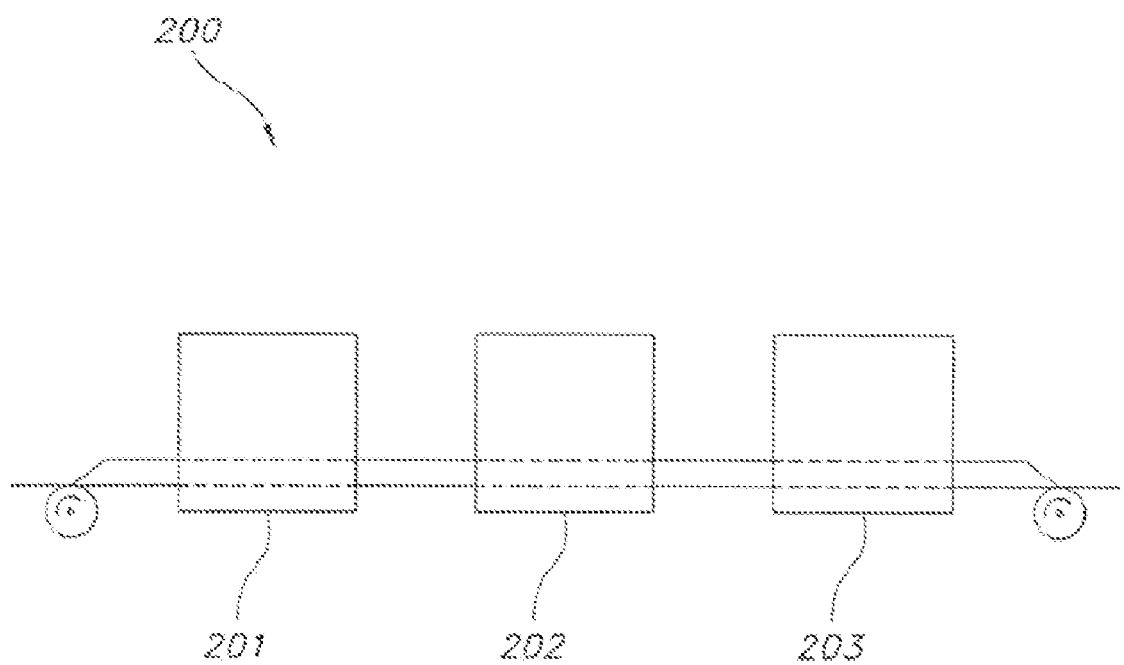
FIG. 10 is a schematic representation of a separate zone drying apparatus in accordance with the present invention.

According to an embodiment of the zone drying apparatus 100, shown in FIG. 9, the film 110 may be fed onto the continuous belt 120, which carries the film through the different drying zones. The first drying zone that the film travels through 101 may be a warm and humid zone. The second zone 102 may be hotter and drier, and the third zone 103 may also be hot and dry. These different zones may be continuous, or alternatively, they may be separated, as depicted by the zone drying apparatus 200 in FIG. 10, where the first drying zone 201, second drying zone 202 and third drying zone 203 are shown. The zone drying apparatus, in accordance with the present invention, is not limited to three drying zones. The film may travel through lesser or additional drying zones of varying heat and humidity levels, if desired, to produce the controlled drying effect of the present invention.

To further control temperature and humidity, the drying zones may include additional atmospheric conditions, such as inert gases. The zone drying apparatus further may be adapted to include additional processes during the zone drying procedure, such as, for example, spraying and laminating processes, so long as controlled drying is maintained in accordance with the invention.

The films may initially have a thickness of about 500 µm to about 1,500 µm, or about 20 mils to about 60 mils, and when dried have a thickness from about 3 µm to about 250 µm, or about 0.1 mils to about 10 mils. In some embodiments, the film product has a thickness of greater than 0.1 mils. In some other embodiments, the film product has a thickness of about 10 mils or fewer. In some further embodiments, the film product has a thickness of about 0.5 mils to about 5 mils. Desirably, the dried films will have a thickness of about 2 mils to about 8 mils, and more desirably, from about 3 mils to about 6 mils.

Testing Films for Uniformity

If may be desirable to test the films of the present invention for chemical and physical uniformity during the film manufacturing process. In particular, samples of the film may be removed and tested for uniformity in film components between various samples. Film thickness and overall appearance may also be checked for uniformity. Uniform films are desired, particularly for films containing pharmaceutical active components for safety and efficacy reasons.

A method for testing uniformity in accordance with the present invention includes conveying a film through a manufacturing process. This process may include subjecting the film to drying processes, dividing the film into individual dosage units, and/or packaging the dosages, among others. As the film is conveyed through the manufacturing process, for example on a conveyor belt apparatus, it is cut width wise into at least one portion. The at least one portion has opposing ends that are separate from any other film portion. For instance, if the film is a roll, it may be cut into separate sub-rolls. Cutting the film may be accomplished by a variety of methods, such as with a knife, razor, laser, or any other suitable means for cutting a film.

The cut film then may be sampled by removing small pieces from each of the opposed ends of the portion(s), without disrupting the middle of the portion(s). Leaving the middle section intact permits the predominant portion of the film to proceed through the manufacturing process without interrupting the conformity of the film and creating sample-inducted gaps in the film. Accordingly, the concern of missing doses is alleviated as the film is further processed, e.g., packaged. Moreover, maintaining the completeness of cut portions or sub-rolls throughout the process will help to alleviate the possibility of interruptions in further film processing or packaging due to guilty control issues, for example, alarm stoppage due to notice of missing pieces.

After the end pieces, or sampling sections, are removed from the film portion(s), they may be tested for uniformity in the content of components between samples. Any conventional means for examining and testing the film pieces may be employed, such as, for example, visual inspection, use of analytical equipment, and any other suitable means known to those skilled in the art. If the testing results show non-uniformity between film samples, the manufacturing process may be altered. This can save time and expense because the process may be altered prior to completing an entire manufacturing run. For example, the drying conditions, mixing conditions, compositional components and/or film viscosity may be changed. Altering the drying conditions may involve changing the temperature, drying time, moisture level, and dryer positioning, among others.

Moreover, it may be desirable to repeat the steps of sampling and testing throughout the manufacturing process. Testing at multiple intervals may ensure that uniform film dosages are continuously produced. Alterations to the process can be implemented at any stage to minimize non-uniformity between samples.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration tunes for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, ophthalmological, the surface of a wound, either on a skin surface or within a body such as during surgery, and similar surfaces.

The films may be used to orally administer an active. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films of the present invention takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

The films of the present invention are desirably packaged in sealed, air and moisture resistant packages to protect the active from exposure oxidation, hydrolysis, volatilization and interaction with the environment. Referring to FIG. 1, a packaged pharmaceutical dosage unit 10, includes each film 12 individually wrapped in a pouch or between foil and/or plastic laminate sheets 14. As depicted in FIG. 2, the pouches 10, 10' can be linked together with tearable or perforated joints 16. The pouches 10, 10' may be packaged in a roll as depicted in FIG. 5 or stacked as shown in FIG. 3 and sold in a dispenser 18 as shown in FIG. 4. The dispenser may contain a full supply of the medication typically prescribed for the intended therapy, but due to the thinness of the film and package, is smaller and more convenient than traditional bottles used for tablets, capsules and liquids. Moreover, the films of the present invention dissolve instantly upon contact with saliva or mucosal membrane areas, eliminating the need to wash the dose down with water.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Example 1

Water-soluble film compositions were prepared using the components set forth in Table 1. The use of low levels of flavors as defoamers in the water-soluble film compositions was evaluated.

TABLE 1

| Component Number | Amount | Weight % | Component |
|---|---|---|---|
| 1. | 24.47 g | 21.96% | Polyethylene oxide |
| 2. | 13.73 g | 10.98% | Hydroxypropyl methylcellulose (15 cps) |
| 3. | 18.50 g | 14.79% | Polydextrose |
| 4. | 3.13 g | 2.5% | Sucralose[1] |
| 5. | 0.63 g | 0.5% | Mono-ammonium glycyrrhizinate[2] |
| 6. | 1.25 g | 1% | Sodium bicarbonate |
| 7. | 2.28 g | 1.82% | Magnesium stearate |
| 8. | 0.63 g | 0.5% | Hydrophilic titanium dioxide |
| 9. | 232.31 g | | Distilled water |

[1]Commercially available from McNeil Nutrition
[2]Commercially available as Magna Sweet 100 from Mafco Worldwide Corp.

Components 8 and 9 were placed in a Degussa 1300 bowl. The components were then processed as described below using the Degussa Dental Multivac Compact.

| 12 minutes | stirring = 500 rpm | vac. = 0% |
| 4 minutes | stirring = 150 rpm | vac. = 0% after added a blend of ingredients 1, 2, 3, 4, 5, 6 & 7 |
| 1 minute | stirring = 100 rpm | vac. = 0% |

The resulting solution was foamy. 20 g of the foamy solution was then added to each of eight 2 ounce wide mouth jars. 0.27 g of glycerol monooleate, a conventional defoaming agent, and the various flavor compounds indicated below were then added to the bottles. (0.27 g would correspond to ~4% in solids of a film).

1. Glycerol monooleate (commercially available as Aldo Mo KFG)
2. Soothing Mist AN143567 (Noville).
3. Orange Burst AN143482 (Noville).
4. Black Cherry SN486305 (IFF)
5. Strawberry SN279913 (IFF)
6. Natural Raspberry 188a10 (Abelei)
7. Cinnamint AN144390 (Noville)
8. Peppermint Bittermask RDW2-193A (Armtodd Co.)

The level of foaminess was then measured as a function of a decrease in the height of the foam within the wide mouth jars. The drop in foam height was measured for the glycerol monooleate jar. This height was used as the measure of effectiveness of the antifoam agents and was set at 100%. Soothing Mint AN143567, Raspberry 188a10, Cinnamint AN144390, and Peppermint Bittermask RDW2-193A gave a decrease in the level of foam equivalent to glycerol monooleate. Orange Burst AN143482 was only ~25% as effective as glycerol monooleate in reducing the foam level. Black Cherry SN486305 and Strawberry SN279913 did not yield any significant reduction in the foam level.

Example 2

Water-soluble film compositions were prepared using the components set forth in Table 2. The efficacy of a foam reducing flavoring agent was compared to conventional defoaming agents.

TABLE 2

| Component Number | Amount | Weight % | Component |
|---|---|---|---|
| 1. | 27.47 g | 21.96% | Polyethylene oxide |
| 2. | 13.73 g | 10.98% | Hydroxypropyl methylcellulose (15 cps) |
| 3. | 18.50 g | 14.79% | Polydextrose |
| 4. | 3.13 g | 2.5% | Sucralose ® (McNeil Nutritionals) |
| 5. | 0.63 g | 0.5% | Mono-ammonium glycyrrhizinate[3] |
| 6. | 1.25 g | 1% | Sodium bicarbonate |
| 7. | 2.28 g | 1.82% | Magnesium stearate |
| 8. | 0.63 g | 0.5% | Hydrophilic titanium dioxide |
| 9. | 232.31 g | | Distilled Water |

[3]Commercially available as Magna Sweet 100 from Mafco Worldwide Corp.

Ingredients 8 and 9 was placed in a bowl and processed as described below using the Degussa Dental Multivac Compact.

| 8 minutes | stirring = 500 rpm | vac. = 0% (using A310 impeller) |
| 5 minutes | stirring = 100 rpm | vac. = 0% (using gate impeller) after added a blend of ingredients 1, 2, 3, 4, 5, 6 & 7 |

The resulting solution was foamy. 20 g of the foamy solution were then added to each of nine 2 ounce wide mouth jars. 0.27 g of the compounds indicated below were then added to the bottles and observed.
1. Glycerol monooleate (commercially available as Aldo Mo KFG)
2. Miglyol® 840
3. Miglyol® 810
4. Miglyol® 829
5. Miglyol® 812
6. Miglyol® 818
7. Vegetable (Wesson® Canola) Oil
8. Isopropyl Alcohol
9. Vicks® Cough Drop Cherry Type F1. AN145163 Miglyol® (Condea Chemie GmbH) samples are clear neutral fatty-acid esters.

The drop in foam height was measured for the glycerol monooleate jar. This height was used as the measure of effectiveness of the antifoam agent and was set at 100%. All other jars was measured as a % of this height. The only compound which gave a significant decrease in level of foam was the cherry flavor. Another sample was tested in which the amount of cherry flavor added was ~25% of that added earlier or 0.0675 g. This sample also gave a significant decrease in level of foam.

Example 3

An edible water-soluble film containing dextromethorphan HBr ($D_x$) as an active ingredient was prepared using 1% cherry flavor as a defoaming agent. (92.3 mg strip contains ~15 mg $D_x$) (35% solids) The components used to form the film are set forth in Table 3.

TABLE 3

| Component Number | Amount | Weight % | Component |
|---|---|---|---|
| 1. | 3.84 g | 21.96% | Polyethylene oxide |
| 2. | 1.92 g | 10.98% | Hydroxypropyl methylcellulose (15 cps) |
| 3. | 2.59 g | 14.79 | Polydextrose |
| 4. | 0.44 g | 2.5% | Sucralose ® (McNeil Nutritionals) |
| 5. | 0.09 g | 0.5% | Mono-ammonium glycyrrhizinate[4] |
| 6. | 0.17 g | 1% | Sodium bicarbonate |
| 7. | 0.32 g | 1.82% | Magnesium stearate |
| 8. | 5.47 g | 31.25% | $D_x$ (52% w/w) 640A 040702W 101-01 (Coating Place, Inc.) |
| 9. | 2.29 g | 13.05% | Vicks ® Cough Drop Cherry Type Fl. AN145163 (Noville) |
| 10. | 0.017 g | 0.1% | Butylated hydroxytoluene (Spectrum Chemicals) |
| 11. | 0.079 g | 0.45% | Cyclohexanecarboximide[5] |
| 12. | 0.17 g | 1% | Vicks ® Cough Drop Cherry Type Fl. AN145163 (Noville) |
| 13. | 0.017 g | 0.1% | FD&C Red #40 |
| 14. | 0.09 g | 0.5% | Hydrophilic titanium dioxide |
| 15. | 32.5 g | | Distilled water |

[4]Commercially available as Magna Sweet ® 100 from Mafco Worldwide Corp.
[5]Acts as a coolant and is commercially available as WS-3 ® from Millennium Chem.

Ingredients 12, 13, 14 and 15 were added to a Degussa 1100 bowl. The solution was then processed as described below using the Degussa Multivac Compact.

| 12 minutes | stirring = 250 rpm | vac. = 0% |
|---|---|---|
| 20 minutes | stirring = 100 rpm | vac. = 50% (13 in Hg) after added a blend of components 1, 2, 3, 4, 5, 6 & 7 |
| 4 minutes | stirring = 100 rpm | vac. = 60% (17.5 in Hg) |
| 4 minutes | stirring = 100 rpm | vac. = 65% (19.5 in Hg) |
| 12 minutes | stirring = 100 rpm | vac. = 70% (20.5 in Hg) |
| 20 minutes | stirring = 100 rpm | vac. = 75% (21.5 in Hg) |
| 4 minutes | stirring = 150 rpm | vac. = 90% (24.5 in Hg) after added a solution compound of 9, 10, & 11 (heated initially at 80° C.) |
| 4 minutes | stirring = 150 rpm | vac. = 100% (27 in Hg) |
| 4 minutes | stirring = 100 rpm | vac. = 100% (27 in Hg) after added ingredient 8 |

The solution was cast into film using the K-control coater with the micrometer adjustable wedge bar set at 530 microns onto 55# ps/l/s "IN" release paper (Griff). The film was dried 17 minutes in an 80° C. air oven. Air moisture was 3.87% as measured by a moisture analyzer (HR73, Mettler Toledo). The film was cut into 23 mm×33.9 mm strips which weighed ~86-98 mg.

The film had no mottling, had good taste, and had no bitterness. The 1% cherry flavor worked well as a defoaming agent.

Thus, while there have been described what are presently believed to be the preferred embodiments of the invention, those skilled in the art will realize that changes and modifications can be made thereto without departing from the spirit of the invention, and it is intended to claim all such changes and modifications which fall within the true scope of the invention.

What is claimed is:

1. A method of preparing an edible water-soluble film composition, said method comprising:
    a) preparing a master batch of film-forming components comprising a water-soluble polymer, a foam reducing flavoring agent selected from the group consisting of menthol, cherry menthol, cinnamint, spearmint, peppermint, orange flavor, natural raspberry, and combinations thereof, and a polar solvent, wherein said foam reducing flavoring agent is added before mixing said polymer with said solvent;
    b) mixing said film-forming components under vacuum;
    c) wet casting said film-forming components; and
    d) removing said polar solvent through a controlled drying process to form said edible water-soluble film;
    wherein said film is free of added defoaming agents.

2. The method of claim 1, wherein the foam reducing flavoring agent is present in amount of about 0.1% to about 20% by weight of the film.

3. The method of claim 1, wherein the foam reducing flavoring agent is present in amount of about 0.5% to about 15% by weight of the film.

4. The method of claim 1, wherein said film composition further comprises an active agent.

5. The method of claim 1, wherein said foam reducing flavoring agent comprises menthol.

* * * * *

UNITED STATES PATENT AND TRADEMARK OFFICE
CERTIFICATE OF CORRECTION

| | | |
|---|---|---|
| PATENT NO. | : 7,972,618 B2 | Page 1 of 1 |
| APPLICATION NO. | : 11/858214 | |
| DATED | : July 5, 2011 | |
| INVENTOR(S) | : Fuisz et al. | |

It is certified that error appears in the above-identified patent and that said Letters Patent is hereby corrected as shown below:

Column 1, line 34:

Now reads:   "sweeteners, plastickers and drugs."

Should read:   -- sweeteners, plasticizers and drugs. --

Column 4, line 25:

Now reads:   "consisting of menthol cherry menthol,"

Should read:   -- consisting of menthol, cherry menthol, --

Column 4, line 38:

Now reads:   "cellulose hydroxypropylmethyl cellulose,"

Should read:   -- cellulose, hydroxypropylmethyl cellulose, --

Column 10, line 34:

Now reads:   "the top air How is the"

Should read:   -- the top air flow is the --

Column 17, line 41:

Now reads:   "about ling to about 200mg"

Should read:   -- about 1mg to about 200mg --

Signed and Sealed this
Twenty-third Day of October, 2012

David J. Kappos
*Director of the United States Patent and Trademark Office*